US010859567B2

(12) United States Patent
Montskó et al.

(10) Patent No.: US 10,859,567 B2
(45) Date of Patent: Dec. 8, 2020

(54) VIABILITY ASSESSMENT OF IN VITRO CULTURED HUMAN EMBRYOS FROM THE CULTURE MEDIUM

(71) Applicant: PÉCSI TUDOMÁNYEGYETEM, Pécs (HU)

(72) Inventors: Gergely Montskó, Pécs (HU); Gábor Kovács, Pécs (HU); József Bódis, Pécs (HU)

(73) Assignee: Pécsi Tudományegyetem, Pécs (HU)

( * ) Notice: Subject to any disclaimer, the term of this patent is extended or adjusted under 35 U.S.C. 154(b) by 426 days.

(21) Appl. No.: 15/313,663

(22) PCT Filed: Jul. 20, 2015

(86) PCT No.: PCT/IB2015/055493
§ 371 (c)(1),
(2) Date: Nov. 23, 2016

(87) PCT Pub. No.: WO2016/009416
PCT Pub. Date: Jan. 21, 2016

(65) Prior Publication Data
US 2017/0102377 A1    Apr. 13, 2017

Related U.S. Application Data

(60) Provisional application No. 62/026,145, filed on Jul. 18, 2014.

(30) Foreign Application Priority Data

Jul. 18, 2014 (EP) ..................... 14462005
Jul. 18, 2014 (HU) ..................... 1400355

(51) Int. Cl.
*G01N 33/50* (2006.01)
*C12N 5/073* (2010.01)
*G01N 33/68* (2006.01)
*G01N 27/416* (2006.01)

(52) U.S. Cl.
CPC ....... *G01N 33/5091* (2013.01); *C12N 5/0604* (2013.01); *G01N 27/4168* (2013.01); *G01N 33/689* (2013.01)

(58) Field of Classification Search
CPC .......... G01N 33/5091; G01N 27/4168; G01N 33/689; C12N 5/0604
See application file for complete search history.

(56) References Cited

U.S. PATENT DOCUMENTS

| 2003/0017515 | A1  | 1/2003  | Ye et al. |
| 2007/0160973 | A1* | 7/2007  | Burns ............... G01N 21/31 435/4 |
| 2007/0254309 | A1  | 11/2007 | O'Neill |
| 2008/0145888 | A1  | 6/2008  | Leese et al. |

OTHER PUBLICATIONS

Weiss et al. "Haptoglobin phenotypes and in vitro fertilization treatment outcomes" (Feb. 2013) Systems Biology in Reproductive Medicine, vol. 59: 281-284. (Year: 2013).*
Keegan et al. "P-229: Direct Matrix Assisted Laser Desorption Ionization (MALDI) Identification of Haptoglobin from culture media of embryos that resulted in a live birth" (2006) Fertility & Sterility, vol. 86, No. 3: S219. (Year: 2006).*
Morbeck et al. "Composition of commercial media used for human embryo culture", (Sep. 2014), Fertility and Sterility: vol. 102, No. 3: 759-766. (Year: 2014).*
Schafer et al. "Redox Environment of the Cell as Viewed through the Redox State of the Glutathione Disulfide/Glutathione Couple" 2001), Free Radical Biology & Medicine, vol. 30, No. 11: 1191-1212. (Year: 2001).*
Feil "Determination of Non-Invasive Viability Markers for Human Embryos in in Vitro Fertilization" (2010), University of Adelaide, Australia (Year: 2010).*

* cited by examiner

*Primary Examiner* — Teresa E Knight
(74) *Attorney, Agent, or Firm* — Jason D. Voight

(57) ABSTRACT

The non-invasive method of assessing the reducing potential of culture medium of in vitro cultured embryos as part of an ART procedure serves as an alternative or supportive method to assess the viability of in vitro cultured embryos without doing any harm to the embryos.

16 Claims, 4 Drawing Sheets
Specification includes a Sequence Listing.

A

B

SEQUENCE LISTING

<160> NUMBER OF SEQ ID NOS: 3

<210> SEQ ID NO 1
<211> LENGTH: 83
<212> TYPE: PRT
<213> ORGANISM: Homo sapiens

<400> SEQUENCE: 1

Val Asp Ser Gly Asn Asp Val Thr Asp Ile Ala Asp Asp Gly Cys Pro
1               5                   10                  15

Lys Pro Pro Glu Ile Ala His Gly Tyr Val Glu His Ser Val Arg Tyr
            20                  25                  30

Gln Cys Lys Asn Tyr Tyr Lys Leu Arg Thr Glu Gly Asp Gly Val Tyr
        35                  40                  45

Thr Leu Asn Asp Glu Lys Gln Trp Ile Asn Lys Ala Val Gly Asp Lys
    50                  55                  60

Leu Pro Glu Cys Glu Ala Val Cys Gly Lys Pro Lys Asn Pro Ala Asn
65                  70                  75                  80

Pro Val Gln

<210> SEQ ID NO 2
<211> LENGTH: 13
<212> TYPE: PRT
<213> ORGANISM: Homo sapiens

<400> SEQUENCE: 2

Thr Glu Gly Asp Gly Val Tyr Thr Leu Asn Asp Glu Lys
1               5                   10

<210> SEQ ID NO 3
<211> LENGTH: 17
<212> TYPE: PRT
<213> ORGANISM: Homo sapiens

<400> SEQUENCE: 3

Ala Val Gly Asp Lys Leu Pro Glu Cys Glu Ala Val Cys Gly Lys Pro
1               5                   10                  15

Lys

VIABILITY ASSESSMENT OF IN VITRO CULTURED HUMAN EMBRYOS FROM THE CULTURE MEDIUM

This is the national stage of International Application PCT/IB2015/055493, filed Jul. 20, 2015, and claims priority to U.S. provisional application Ser. No. 62/026,145, filed Jul. 18, 2014, the entire disclosures of which are hereby incorporated by reference herein.

FIELD OF THE INVENTION

The invention relates to in vitro methods for non-invasive embryo viability assessment during assisted reproduction.

BACKGROUND ART

Infertility affects a relatively high percentage of the mature population leading to an increasing need of the use of assisted reproductive technologies (ART), and in vitro fertilization (IVF). Since the first reported case and introduction of IVF by Steptoe and Edwards the technology became more and more widespread resulting in 125,000 cycles a year in the US in 2007. The total number of ART cycles in Europe was 493,184 in 2007, while in 2008 and 2009 this number reached more than 500,000 cases (1). The development of microsurgical technologies such as the intracytoplasmatic sperm injection (ICSI) means that most couples have the chance of successful fertilization. Other improvements like new culture media, advances in cell culturing conditions result in the ability to culture human embryos in vitro till even the blastocyst stage is achieved meaning 5-7 days. All factors mentioned theoretically suggest a high success rate among IVF experiments in the practice, however, it is far below the expectations. The rate of the successful embryo implantations is surprisingly low (2). In 1995 Dawson et al. (3) reported a success rate of 25%, while in 2004 Scott (4) reported a 27.7% successful delivery rate. In 2009 in Europe this rate went up to 32% depending on the used ART technology (1).

To overcome this limitation of Art, often multiple embryos are transferred in a single cycle (5). Multiple embryo transfer however increases the chance of multiple pregnancies, which has undesired consequences. Multiple gestations can result in the increased risk of preterm delivery accompanied by low birth weight, and the risk of cerebral palsy or lifetime disabilities (4). In 2008 preterm births resulting from multiple pregnancies during IVF caused a 1 billion USD extra cost to the social insurance in the US (5). Due to these considerations the trend is to transfer fewer embryos, though this results in a lower success rate, which is the most criticized aspect of IVF (6). According to the present consensus the best option might still be the single embryo transfer if embryo viability could be assessed prior the transfer.

The goal therefore is to find reliable morphological and/or biochemical markers to assess the embryo without doing any harm to it and predict the implantation potential. This way we would be able to avoid the health risks of multiple births without sacrificing the chances of a successful pregnancy. The easiest and most obvious way to predict embryo viability is by scoring the embryo using morphological markers. These markers include blastomere size, the symmetry and rate of embryo cleavage (18), cumulus-coronal cell morphology, cytoplasm granularity and embryo polarity. Assessing Morphological markers also include the examination of early pronuclear breakdown (2) and chromosome morphology. The main problem with these embryo morphology based techniques is that even embryos described with the best aspect tend to result in unsuccessful pregnancy, or lead to spontaneous abortion in a rate that cannot be explained by maternal reasons alone (7). A possibly better option is the use of molecular markers, such as gene expression profile (8), RNA expression of targeted genes (7) the detection of aneuploidy or the examination of chromosomal complement. The other approach is the metabolomic analysis of the embryo using the culturing media, by selecting targeted compounds, or by analyzing the total metabolome (9).

Targeted analysis is conventionally achieved by the measurement of glucose and pyruvate uptake or the measurement of amino acid turnover. Some authors reported that the identification of these parameters resulted in successful prediction of embryo implantation potential, but some studies describe contradictory results. There is a strong consensus that more than one metabolomic parameters should be analysed, and currently the best approach seems to be the measurement of the total metabolome (10). Analytical tools cover near infra-red spectroscopy, Raman spectroscopy, and more recently mass spectrometry (7). Mass (MS) spectrometry has the potential of specific and sensitive quantification in a wide spectrum of molecular mass ranges and therefore suites well the needs of metabolomic or proteomic fingerprinting and quantification.

According to the current protocols, the viability of the embryo during the IVF process is assessed by microscopic inspection, resulting in a pregnancy rate of 25-30%.

In addition, EP1847595A1 discloses an in vitro method for non-invasive embryo viability assessment comprising the detection of the proteins p53, Cav12 or catalase in the embryo culture medium as biomarkers.

Haptoglobin (Hp) is a tetrameric protein secreted by the liver and involved in binding free haemoglobin. The mature protein molecule consists of two disulfide linked α and β chains. The chains originate from a common precursor protein, which is proteolytically cleaved during protein synthesis.

Haptoglobin has been found in all mammals studied so far and in its simpler form, in bony fishes. It appears to be present in some birds, but being absent from neognathous birds and from at least some amphibians (*Xenopus*).

The quaternary structure of haptoglobin in organisms other than humans typically consists of a dimer of alpha-beta-chains covalently linked by a disulphide bridge between the Cys15 residue of each alpha-chain. However, in humans the β chains are identical in all haptoglobin types (glycosylated 40 kDa, 245 amino acids; unglycosylated 35 kDa) while the α chains have two allelic forms in humans, alpha-1 and alpha-2, determining three possible genotypes. When haptoglobin is synthesized as a pre-protein it is cleaved by the endoplasmatic reticulum to the mature peptide containing two alpha and two beta chains connected by a disulphide bond (11). Haptoglobin can be fragmented into the alpha and beta chains by the cleavage of the disulphide bond via cleaving enzymes or chemical reduction.

The protein structure is constituted by monomers assembled by one subunit of α and one subunit of β, disulfide bonds hold together the two subunits (12). The β subunit (40.0 kDa) is invariant; however two α alleles, namely α1 subunit (8.9 kDa) and α2 subunit (16.0 kDa) exist. Since α1 and α2 form one and two intermonomer bonds, only the dimer βα1-βα1 (phenotype Hpt 1-1) is present in the homozygous Hp1/Hp1, while a population of circular isoforms with βα2 monomers (phenotype Hpt 2-2) is present in the homozygous Hp2/Hp2. The heterozygous Hp1/Hp2 displays linear chains of βα2 monomers, end-capped with βα1 monomers (phenotype Hpt 1-2). The structure of haptoglobin is shown on FIG. 4, taken from (13). In the literature, the nomenclature of haptoglobin and zonulin is ambiguous, most probably zonulin is the Pre-HP2 pre-haptoglobin isoform.

Human haptoglobin is known to accumulate in HSA (human serum albumin) standards used in cell culture media during HSA purification (14). The human haptoglobin alpha-1 chain is a 9186.5 Da protein present in HSA supplemented cell culture medium used for culturing human embryos. The source of the haptoglobin alpha-1 fragment in the HSA standard and finally in the culture medium can be the cleavage of the disulphide bond connecting the alpha and beta chains of the mature haptoglobin-1 molecule (15).

A specific detection of Haptoglobin-alpha 1 Subunit is described e.g. in US 2003/0017515 A1 and in (16) by an epitope-specific binding molecule for detecting the level of the fragment of haptoglobin (i.e. a polyclonal antibody against HP-alpha).

Haptoglobin was hypothesized as a marker for embryo viability in (17). it is disclosed the presence of haptoglobin plays a role in implantation of the embryo and thus correlating with successful pregnancy.

SUMMARY OF THE INVENTION

The present invention provides a more accurate non-invasive embryo viability assessment by
a) assessing the reducing potential of an embryo culture medium;
b) comparing said reducing potential to a predetermined reducing potential;
c) identifying the embryo cultured in said medium as being inappropriate for resulting in successful pregnancy, wherein said reducing potential is above said predetermined level.

In one preferred embodiment, the present invention is aimed at providing a more accurate non-invasive embryo viability assessment by quantitation of the alpha-1 fragment of human haptoglobin, which was found to be present in a significantly greater amount in the culture medium of non-viable than of viable embryos cultured in vitro as a part of the ART process. According to our measurements in the group of culture media of embryos, which were assigned in the biochemical assay as non-viable (based on the amount of the haptoglobin fragment) there were no pregnancies detected, thus this assay revealed a 100% successful selection of the non-viable embryos. In the group assigned as viable, the rate of birth was 54%.

In this aspect of the invention, a test sample of an embryo culture medium and a control culture medium without the embryo is provided; both the embryo culture medium and the control culture medium comprising haptoglobin, a fragment of haptoglobin is detected in the test sample and in the control sample; wherein a higher level of said haptoglobin fragment in the test sample as compared to the control sample is indicative of an embryo in the embryo culture medium, said embryo having a limited chance or being inappropriate for resulting in successful pregnancy.

Thereby those embryos having a limited chance or being inappropriate for resulting in successful pregnancy, may be considered as non-viable and can be selected out from a set of embryos and the rest of them may be considered as viable for the object of the present invention (unless considered as non-viable by any other method). Thereafter preferably only an embryo considered as viable may be used for implantation. Thereby the rate of successful pregnancy is significantly higher than without pre-selection.

Haptoglobin was hypothesized as a marker for embryo viability in (17). It is disclosed that the presence of haptoglobin plays a role in implantation of the embryo and thus correlating with successful pregnancy. Accordingly, (17) teaches away from the present invention.

With respect to the embodiment involving the measurement haptoglobin fragments/subunits, EP1847595 may be considered as the closest prior art. It discloses a very generic assay for determining the viability of an embryo by culturing an embryo in vitro in culture medium; measuring the level of a marker in the culture medium; and comparing the measured level of the marker in the culture medium to at least one level of the marker which is indicative of the viability of the embryo and thereby determining the embryo viability. No indication is there that haptoglobin could be used as said marker. The person skilled in the art would not have reasonable expectation of success to replace haptoglobin into this method and obtain credible results.

One embodiment of the present invention provides a non-invasive embryo viability assessment, wherein said reducing potential is assessed in step a) by monitoring during culturing the embryo.

Another embodiment of the present invention provides a non-invasive embryo viability assessment, wherein said reducing potential is assessed in step a) in a sample taken from the culture medium after the removal of the embryo.

In a preferred embodiment of the invention, said reducing potential is assessed by direct measurement.

In another preferred embodiment of the invention, said direct measurement is performed by a redox electrode.

In another preferred embodiment of the invention, said reducing potential is assessed by detecting the reduction of a reducible compound present in said sample taken in step a).

In another preferred embodiment of the invention, said reducing potential is assessed by detecting the reduction of a reducible compound added to said sample taken in step a) after the removal of the embryo.

In another preferred embodiment of the invention, said sample taken in step a) is kept under conditions allowing said reducible compound to be reduced.

In another preferred embodiment of the invention, said reducible compound contains at least one disulphide bond.

In a specific embodiment of the invention, said reducible compound is selected form the group consisting of macromolecules, peptides and small molecules, and preferably is haptoglobin, glutathione disulfide (GSSG), oxidized mercapto-succinic acid or oxidized mercapto-butanol.

In another preferred embodiment of the invention, the reducing potential is indicated by a detectable amount of a reduced form of said reducible compound.

In another preferred embodiment of the invention, the reducing potential is indicated by a numerical redox potential value.

In further preferred embodiment of the invention, said predetermined reducing potential is determined by
i) culturing a pool of embryos in embryo culture medium;
ii) assessing the reducing potential of the culture mediums of each embryos in said pool;
iii) retrospectively correlating the reducing potential assessed in step ii) of each embryo culture medium to successful pregnancies resulted from implanting the embryos cultured in said culture medium; and iv) determining said predetermined reducing potential as the highest level of reducing potential wherein successful pregnancy was observed.

In another preferred embodiment of the invention, said assessment in step ii) is done by direct measurement or by detecting the reduction of a reducible compound.

In another preferred embodiment of the invention, said assessment in step ii) is done by detecting the reduction of a reducible compound and said highest level of reducing potential in step iv) is indicated by the non-detectability of the reduction of said reducible compound.

In a preferred embodiment, the fragment of the haptoglobin molecule is a reduced haptoglobin fragment obtained by reduction of a disulphide bond between alpha and beta chains of haptoglobin, said fragment having a sequence specific for said haptoglobin chain.

Preferably, the fragment of the human haptoglobin is selected from a haptoglobin alpha fragment and a haptoglobin beta fragment. Preferably the haptoglobin alpha fragment is a haptoglobin alpha-1 fragment.

In an embodiment, in the method according to the invention detection of said fragment of haptoglobin is carried out by an assay method selected from the group consisting of
mass spectrometry,
immunoassay,
a spectroscopic method
a functional test,
a sequencing method or a combination thereof.

Any method used for detection should preferably be specific for the fragment of haptoglobin the level of which is to be detected.

Preferred methods are mass spectrometry and immunoassays.

Immunoassays include any method wherein an epitope-specific binding molecule is applied to detect the level of the fragment of haptoglobin according to the invention. Such epitope-specific binding molecules include antibodies e.g. monoclonal antibodies and antibody fragments and molecules having a binding region appropriate for binding to an epitope, like minibodies and antibody mimetics, like affibodies, anticalins, monobodies etc.

Preferred assays are ELISA, Western-blot etc. There are many practical approaches for carrying out these types of assays. The preferred ones are those that are easily automated, such as chip-type assays (an example of which is shown at http://www.raybiotech.com/quantibody-multiplex-elisa-array.html). Similarly, wick-strip type assays may be also developed for the immunoassay embodiments.

It is envisaged a chip-bound enzyme-linked-immunoassay (ELISA) test based on a specific monoclonal antibody raised against the alpha-1 subunit of human haptoglobin. A first antibody is bound to glass or polycarbonate chip surface. After the application of a sample of the embryo culture medium (viable, non-viable, and control, in the following all are referred to as "sample") a washing step will be done to avoid aspecific staining, and afterwards the reaction will be quantified using a second antibody in solution containing a chromophore moiety. The reaction is detected using a chip reader in UV, VIS or fluorescent light depending on the characteristics of the labeling moiety.

In a preferred embodiment a separation step of separating said fragment from the test sample and from the control sample is carried out before the detection of the fragment. This separation step also can be utilized to make the method fragment-specific, if resolution of the separation is sufficiently high to separate the haptoglobin fragment to be detected from other haptoglobin fragments or proteins interfering with the measurement.

Separation can be performed based on any molecular property in which the fragments differ and which is suitable to achieve a sufficient separation, like size, charge, hydrophobicity, isoelectric point, affinity, etc.

For example in a Western-blot experiment an electrophoretic step may precede the blotting step resulting in a separation of the fragments.

A preferred practical solution for the separation is a chip based microfluidic gel electrophoresis an example of which is shown at http://www.perkinelmer.com/catalog/product/id/760528). The electrophoretic poly-acrylamide (PAGE) gel is miniaturized to a chip, containing microfluidic channels Sample analysis is performed in a combined instrument which performs the electrophoretic separation of the sample in parallel to the detection and quantification of the results. Alpha-1 subunit of human haptoglobin is aspecifically labeled using a chromo- or fluorophore dye. Specificity is achieved using the known molecular mass of the alpha-1 subunit of human haptoglobin. In contrast to other already existing products the developed chip will be capable to separate a mass range specifically designed for embryo culture medium analysis.

In a preferred embodiment of the method if the level of the haptoglobin fragment in the test sample is higher than that of the control sample and is equal at least with a threshold value, preferably a pre-determined threshold value, this fact is indicative of a limited chance of the embryo for or being inappropriate for resulting in successful pregnancy.

In a preferred embodiment of the method if the level of the haptoglobin fragment in the test sample is at least 110%, 115%, 120%, 125%, 130%, 135% or 140% of that of the control sample, the embryo is classified non-viable. Optionally, if the level of the haptoglobin fragment in the test sample is under 110%, 115%, 120%, 125%, 130%, 135% or 140% of that of the control sample the embryo is classified viable.

In a preferred embodiment the threshold value is pre-determined experimentally.

In an embodiment levels in case of embryos resulting in birth is compared with levels in case of embryos which do not result in birth.

In an embodiment, the threshold is set to a value wherein embryos for which the level is lower than the threshold do not result in birth in 100% of the implantations (cycles).

In another embodiment, the threshold is set to a value wherein embryos for which the level is at least equal to the threshold result in birth in at least 40%, 50%, 60%, 70%, 80% or 90% of the implantations (cycles).

In a preferred embodiment the embryo is a mammalian, preferably a human embryo. Highly preferably the embryo is a human embryo.

In a preferred embodiment the haptoglobin is a mammalian, preferably a human haptoglobin. Highly preferably the haptoglobin is a human haptoglobin.

In a preferred embodiment the embryo is a human embryo, the haptoglobin is a human haptoglobin, and the haptoglobin fragment is selected from a group consisting of a haptoglobin beta fragment, haptoglobin alpha fragment, haptoglobin alpha-1 fragment, haptoglobin alpha-2 fragment, a haptoglobin alpha-beta fragment, haptoglobin alpha-1-beta fragment, haptoglobin alpha-2-beta fragment; preferably from a group consisting of a haptoglobin beta fragment, haptoglobin alpha-1 fragment, haptoglobin alpha- 1-beta fragment, preferably from a haptoglobin alpha-1 fragment or a fragment comprising multiple fragments, however, less fragments than the whole haptoglobin.

In a preferred embodiment both the sample and the control culture media comprise serum albumin.

In a preferred embodiment the non-invasive embryo viability assessment method of the invention is combined with another non-invasive embryo viability assessment method. Preferably, if the embryo is assessed to be non-viable based on any of the methods it is not selected for implantation. Preferably, if the embryo is assessed to be viable based on each of the viability assessment methods, it is selected for implantation. Preferably, the method for non-invasive embryo viability assessment is combined with the microscopic evaluation of embryo viability based on embryo morphology.

In a further aspect the invention also relates to a method for in vitro fertilization of a female patient, wherein the method comprises the embryo assessment method of the invention, and the additional step of implanting at least one embryo into the uterus of a female patient. Preferably, the female patient is a fish, bird or a mammal having haptoglobin. More preferably, the female patient is a mammal. Even more preferably the female patient is a human.

In a further aspect the invention also relates to a use of an embryo culture medium for non-invasive embryo viability assessment by measuring the level of a haptoglobin fragment as defined herein, said medium comprising haptoglobin.

In a further aspect the invention also relates to the use of a haptoglobin fragment as defined herein for non-invasive embryo viability assessment.

In a further aspect the invention also relates to the use of a detectable binding molecule capable of specifically binding to a fragment of a haptoglobin as defined herein for non-invasive embryo viability assessment.

Preferably non-invasive embryo viability assessment is carried out by a method for non-invasive embryo viability assessment as defined herein.

In a further aspect the invention relates to kits for determining the level of a haptoglobin fragment containing ready-to-use immunoassay(s) containing an epitope-specific binding molecule for detecting the level of a fragment of haptoglobin according to the invention.

In an embodiment a kit contains culture medium suitable for embryo culturing with a predetermined haptoglobin content.

In a preferred embodiment the kit contains culture medium suitable for embryo culturing with a predetermined haptoglobin content and a ready-to-use immunoassay as defined above.

In a highly preferred embodiment the kit is in the form of a chip suitable to carry out various biochemical measurements simultaneously.

Definitions

The term "embryo" as used herein refers to an embryo, preferably a human embryo in the first stage of development, between the fusion of gametes and the blastocyst stage. The term "embryo" as used herein refers to the morula stage of the development of an embryo. Also, the term "embryo" as used herein refers to an in vitro fertilized and cultured embryo prior to implantation.

The term "viable" when used herein referring to an embryo refers to an embryo that is not identified as an embryo that has limited or no chance of implantation based on the level of reducing potential, or based on any further indicator that shows said change in the reducing potential level. Such indicator may be a level of haptoglobin below a pre-determined threshold level indicating that the embryo is not impaired and may be appropriate for implantation. Preferably, the in vitro culture medium of the embryo contains less than 110%, 120%, 130%, 140% or 150% of the amount of a haptoglobin fragment of the control culture medium not comprising the embryo. On the contrary, increased level of a haptoglobin fragment may indicate that the embryo is inappropriate for implantation and for resulting in successful pregnancy.

Nevertheless, the implantation of a viable embryo into the uterus of a female patient may or may not result in successful pregnancy and/or may or may not result in live birth, as these results depend on many other factors. On the contrary, the implantation of a non-viable embryo will not result in successful pregnancy. Successful pregnancy is understood as reaching delivery stage.

Accordingly, the chance for implantation of viable embryos and thus successful pregnancies are improved by the fact that definitively non-viable embryos are eliminated with certainty. Therefore the person skilled in ART will be able to implant fewer embryos to avoid later complications, as detailed above.

"Reduction potential" (also known as redox potential, oxidation/reduction potential) is a measure of the tendency of a chemical species to acquire electrons and thereby be reduced. Reduction potential is measured in volts (V), or millivolts (mV). Each chemical species has its own intrinsic reduction potential; the more positive the potential, the greater the species' affinity for electrons and tendency to be reduced. The term "reducing potential" has a broader meaning as used herein, it indicates that a compound or a mixture (e. g. a complex biological system, i.e. the mixture of an embryo and the culture medium thereof) is capable of reducing another chemical species. It may be a qualitative measure rather than quantitative. Since the other chemical species, that is reducible by the compound or mixture that has a specific "reducing potential", has a redox potential value of their own, therefore said compound or mixture may be also assigned a redox potential value. Direct measurement of the "reducing potential" through the measurement of this reduction potential can be carried out by standard techniques, such as by using suitable electrodes. The "reducing potential" signifies the capability to reduce and is specific for a given environment.

The term "reducible compound" is not limited if its redox potential may change under the conditions of the embryo culture medium.

The term "predetermined cut-off value" means a reducing potential level above of which the embryos are assessed as non-viable by retrospective correlation studies. It is not necessarily a definitive numerical value, it may be indicated by the identity of a reducible/indicator compound that is reduced under the conditions of the embryo culture medium from its oxidized form. As the person skilled in the art will know, the oxidized form may not be converted fully into the reduced form, since there is an equilibrium of these chemical reactions. therefore, for a given reducible compound, a threshold level or ratio may be given for the reducible form, above of which the reduction deemed to taken place.

"Haptoglobin" is a multimeric protein having subunits linked by disulphide linkages, and being expressed as a precursor polypeptide chain (zonulin) and processed into alpha and beta chains Haptoglobin belongs to the peptidase S1 family and contains a peptidase S1 domain and sushi (CCP/CCP) domains Preferably haptoglobin according to the invention shows at least 30%, 40%, 50%, 60%, 70%, 80% or 90% sequence identity with a fish, bird or mammalian, preferably mammalian haptoglobin sequence e.g. a human haptoglobin sequence. Mammalian sequences are given e.g. in the UniProtKB/Swiss-Prot database, e.g. on the following reference numbers: P00738; G3RSR8; J3QR68; H2RAT6; G3RB80; P00738-2; Q28800; Q28803; G3S6B1. Haptoglobin is encoded by the HP gene (in humans) or a gene corresponding thereto. Preferably native haptoglobin functions to bind free plasma haemoglobin, what allows degradative enzymes to gain access to the haemoglobin while at the same time preventing loss of iron through the kidneys and protecting the kidneys from damage by haemoglobin.

A "haptoglobin fragment" is a part of the haptoglobin molecule consisting of a shorter chain and/or a subunit thereof or both. The terms "fragment" and "subunit" are to be used interchangeably herein. The term "fragment" does not include any chains of amino acids resulting from random breakage of the polypeptide chain, or synthetic fragments based on the sequence of haptoglobin that are not produced in vivo.

A "reduced fragment" of a multi chain protein is obtained by reduction of a disulphide bond between chains of said protein, said fragment having a sequence specific for said chain. Thus, a "reduced haptoglobin fragment" is a fragment obtained by reduction of a disulphide bond between subunits of the haptoglobin, said fragment having a sequence specific for said haptoglobin chain.

In the present invention mutated haptoglobin subunit, fragment or chain sequences are contemplated provided that their sequence is at least 30%, 40%, 50%, 60%, 70%, 80% or 90% identical with native fish, bird or mammalian sequences calculated with reference to the full length of the native sequence of the subunit, fragment or chain, and wherein with a detection method such mutated sequence is detected together with the native subunit, fragment or chain. Thus, a mutated sequence is to be understood as including any difference including substitutions, deletions and optionally additions. Thus, fragments having a shorter chain length are contemplated so far they can be detected together with and/or specifically to the native subunit, fragment or chain.

The "haptoglobin alpha-1 chain" refers to the full length chain of a haptoglobin alpha-1 subunit. The terms "haptoglobin alpha-1 fragment", "haptoglobin alpha-1 subunit", and "haptoglobin alpha-1 chain" are used interchangeably. The term "haptoglobin alpha-1 fragment" may be understood as a "haptoglobin alpha-1 chain" and, as used herein, also may refers to any fragment of the haptoglobin alpha-1 chain, that has an amino-acid sequence specific to said chain and is generated from the original haptoglobin alpha-1 chain in vivo. This refers to mutates mutandis to other subunits. The person skilled in the art will be able to assess without undue burden whether a specific haptoglobin alpha-1 fragment/subunit/chain is generated in vivo by carrying out simple model experiments with the original natural or mutated haptoglobin alpha-1 chain in the culture medium being used, and analyzing the resulting polypeptide sequences.

A "sample" of a substance, e.g. culture medium means a part or a whole (e.g. whole part) of said substance which is appropriate for handling in an experiment or assay.

As used herein, in a broader sense, a "part" of an entity is understood as also including the whole entity unless otherwise specified, whereas said entity is composed of one or more parts. A fragment is a part which does not involves the whole. In a narrower sense a part is a fragment of the whole entity. Preferably, a fragment is a part which is specific to the whole entity. In an aspect one or more parts make up the whole entity.

A "culture medium" as used herein is a substance useful and appropriate for culturing cells, either separate cells or cells attached to each other or a tissue. In a preferred embodiment the culture medium is an embryo culture (or culturing) medium appropriate for culturing an embryo, preferably from the one cell stage to the blastocyst stage. Preferably the embryo is a fish, bird or mammalian embryo, preferably a mammalian embryo, highly preferably a human embryo.

A "higher level" of a substance in a first sample than in a second sample indicates that the level, depending on the method for measuring and, if appropriate, calculating said level, including optionally the statistical method involved, is noticeably, detectably or significantly higher in the first sample than in the second sample. Preferably "higher level" means that the level is above or is at least equal to a threshold value, e.g. as defined herein.

"Detection" involves a technical method wherein a substance is detected in a sample and includes or comprises quantitative or semi-quantitative detection; thus, the term can be understood as including measuring, assessment and/or calculation steps or a combination thereof as required to obtain the desired information. Thus, in a preferred version, detecting means measuring and/or assessing.

As used herein the singular forms "a", "an" and if context allows "the" include plural forms as well unless the context dictates otherwise.

The term "comprises" or "comprising" or "including" are to be construed here as having a non-exhaustive meaning and allow the addition or involvement of further features or method steps or components to anything which comprises the listed features or method steps or components.

The expression "consisting essentially of" or "comprising substantially" is to be understood as consisting of mandatory features or method steps or components listed in a list e.g. in a claim whereas allowing to contain additionally other features or method steps or components which do not materially affect the essential characteristics of the use, method, composition or other subject matter. It is to be understood that "comprises" or "comprising" or "including" can be replaced herein by "consisting essentially of" or "comprising substantially" if so required without addition of new matter.

DETAILED DESCRIPTION OF THE INVENTION

Figure 1:
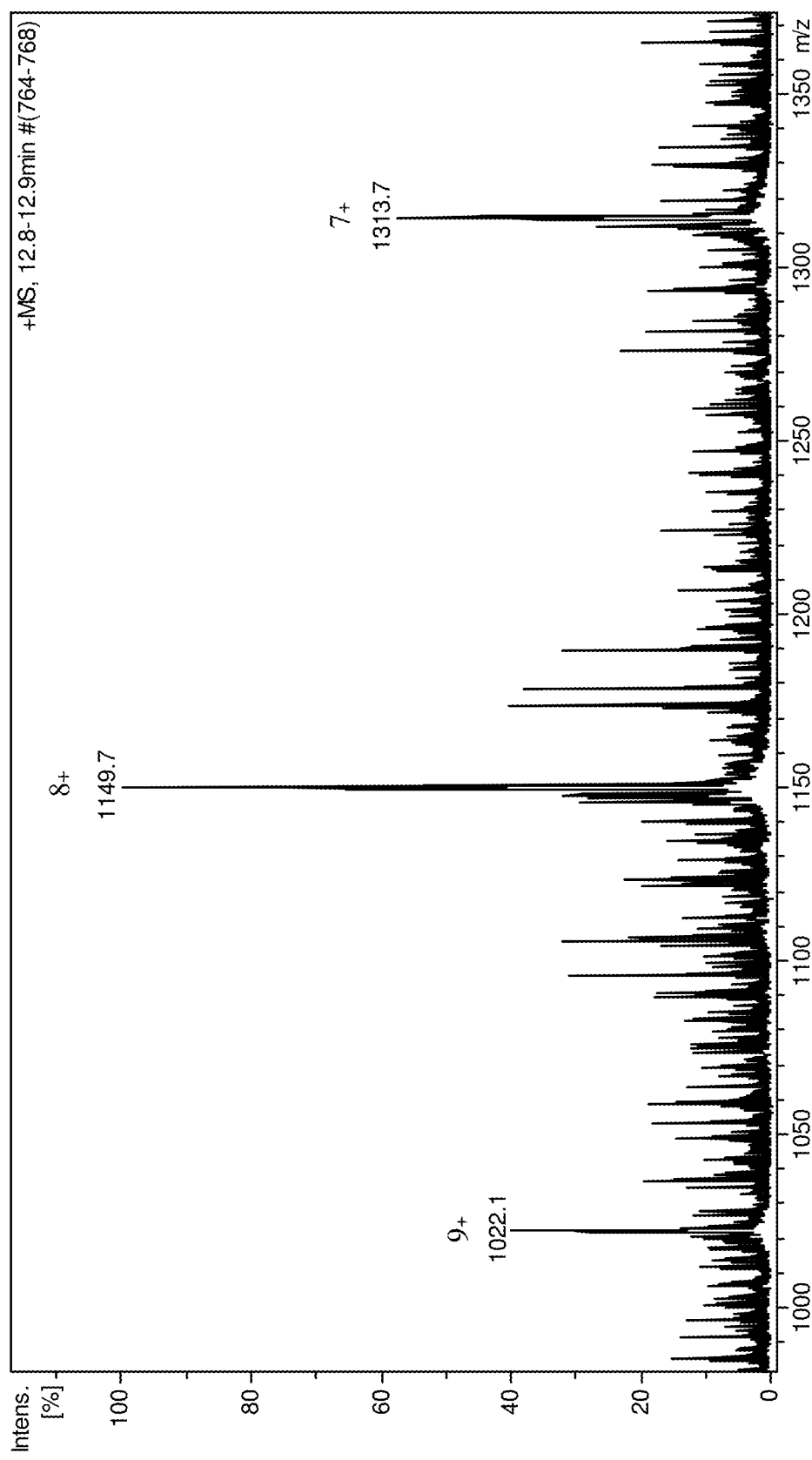
FIG. 1 Mass spectrum of the identified haptoglobin fragment. The most intensive ion at m/z 1149.7 m/z corresponds to the $[M+8H]^{8+}$ ion of the molecule. The ones at m/z 1022.1 and m/z 1313.7 are the other two multiply charged ions $[M+7H]^{7+}$ and $[M+9H]^{9+}$ detected with acceptable signal to noise ratio.

Viability assessment prior embryo transfer is a crucial question since the success rate of IVF interventions is surprisingly low worldwide. The practice of multiple embryo transfer to overcome this limitation is accompanied by several risk factors leading to a consensus that the best option is the single embryo transfer (32) where the implantation potential of the embryo could be assessed in vitro during the first couple of days of development. Rather than the routinely used embryo morphology based approaches like cleavage rate, or blastocyst symmetry, measurement of the metabolomic processes of the developing embryo, or the search for biomarkers in the cell culture medium seems to be a better option. The aim of our work was to find any biomarker present in the embryo culture medium using mass spectrometry, which would qualitatively or quantitatively differ in the samples of viable and non-viable embryos.

We have unexpectedly found that the amount of a fragment of a polypeptide present in the culture medium conventionally used for culturing embryos as part of the IVF process has increased in the culture media of embryos that later proved to be non-viable, i.e. the implantation of which did not result in successful delivery, compared to the amount of the same fragment measured in the culture media of embryos proved to be viable and in control culture media without an embryo. We identified the said fragment as the human haptoglobin alpha-1 fragment, derived from the protein haptoglobin by way of the cleavage of the disulphide bond connecting the alpha and the beta chain of the haptoglobin molecule.

During pre-implantation the number of embryonic cells increases; however this increase is the result of cell proliferation and cell death. In contrast to normally developing embryos the ones with lower viability show a higher rate of apoptosis similar to the arrested embryos, finally resulting in secondary necrosis and an increase in membrane permeability (18). Apoptosis involve the activation of proteases and other enzymes, which due to membrane disintegration might be released into the culturing medium. When cell membrane disintegration accompanying cell death happens, these activated proteolytic enzymes leave the cell and start cleaving proteins found in the culture media.

When haptoglobin is synthesized as a pre-protein it is cleaved by the endoplasmatic reticulum to the mature peptide containing one alpha and one beta chain connected by a disulphide bond (11). In a reducing chemical environment this bond can break, forming two sulfhydryl groups. The explanation for the increased amount of this alpha-1 fragment in the samples of unsuccessful embryos might be the fact that abnormally developing embryos often show the characteristics of apoptosis in a larger extent than normal embryos, later followed by secondary necrosis accompanied by increased membrane permeability (18).

We suggest that during its development the non-viable embryo changes the chemical composition of the culture medium to a more reducing environment, thus causing the increased cleavage or reduction of the disulphide bond connecting the alpha and beta chain of haptoglobin. The processes of apoptosis and finally necrosis accompanied by an increase in membrane permeability and the changes in the chemical composition of the culture medium may result in the increase of the amount of several polypeptide fragments cleaved by the activated proteolytic enzymes from proteins of the culture medium. This may happen only in the culture media of abnormally developing embryos as the level of apoptosis is lower in normally developing embryos. Along with the amount of the alpha-1 fragment of the human haptoglobin protein, the amount of the β chain or the amounts of shorter fragments specific to this protein may increase. The fact that disulphide bond cleavage is the source of the haptoglobin alpha 1 fragment was confirmed in our experiment where the disulphide bond reducing agent dithiothreitol was added to the control (no embryo containing) G1+HSA medium and an increase was observed in the amount of the alpha-1 fragment. The presence of free thiol groups was confirmed by the addition of 2-iodoacetamide, an alkylating agent of thiol groups. in the light of the above described process of apoptosis observed when an embryo develops abnormally, we suggest that proteins of the culture media of a embryo cultured in vitro as part of an IVF process, and in particular haptoglobin are fragmented by cleaving enzymes or chemical reduction and these fragments can be detected, quantified and thus used as indicators of abnormal development. Such fragments can be identified prior to the implantation of the embryo from a sample of the culture medium, without doing any harm to the embryo, by methods well known in the art, e.g. by HPLC. The amount of such fragments can be quantified and compared with the amount of fragments in a control sample likewise by methods well known in the art, such as mass spectrometry or various immunoassays.

In addition to reduction of the disulphide bond connecting the native alpha and beta chain of haptoglobin, other mutated versions of haptoglobin may be contemplated provided that the reducible disulfide bond(s) are present.

To further the above hypothesis based on the originally observed phenomenon, namely the reduction of the disulphide bond leading to the fragmentation of the human haptoglobin molecule, we designed further experiments to see whether is specific to haptoglobin, or is universal. The embryo undergoing increased apoptosis has a reducing environment that may affect further molecules containing disulphide bonds. It is clear that no any new compounds may be added to the embryo culturing media because of ethical issues. However, it is evident that that the reducing potential causing the disulphide bond reduction within the haptoglobin molecule is still preserved after the embryo is removed from the incubation medium.

As shown in the examples, haptoglobin serves as a macromolecular example originally present in the embryo culture medium. However, other disulphide containing macromolecules may be added to the medium after the removal of the embryo, and its reduction may be similarly observed.

Specific embodiments of this aspect may employ any type of compound that may be easily reduced at the range of redox potential of the embryo culture medium when the embryos are cultured and may deteriorate and result in non-viable embryos. This range of reducing potential may be measured several ways. Either direct measurements are possible (with a suitable electrode) or an indirect assessment of the reducing potential is also envisaged. In the latter technique, a series of reducible compounds are tested for reduction by the embryo culture medium, and then analyzed (including retrospectively compared to live births) whether the reduction of the specific compounds took place or not in the samples. Thereby the assessment of the viable embryos may be carried out by establishing a cut off level, which e.g. may be defined as a definitive compound of the above calibration series which is cleaved/reduced at the reducing potential level that is capable of differentiating viable and non-viable embryos.

Shorter peptides or even small molecules are known for the person skilled in the art and may be chosen as reducible compound. Exemplary reducible compounds are redox indicators, or preferably disulphide containing compounds. In the present specification, test compounds were gluthathione disulphide, a peptide composed of six amino acids and mercapto succinate disulphide, a mercaptocarboxylic acid. As shown below in the examples, both were successfully used to distinguish between viable and non-viable embryos based on the analysis of the spent culture medium after embryo-removal. The person skilled in the art will be able to choose from a large set of reducible compound available commercially. Reducible compounds may be macromolecules, peptides, small molecules. A preferable macromolecule is haptoglobin, as detailed elsewhere in the description. Other examples are oxidized molecules the reduced form of which contains free sulfhydryl groups. Detection and measurement of free sulphydril groups is well known in the art.

As practical solutions, chip, microtiter plate or micro test tube based assay exist to detect the conversion of oxidized glutathione (GSSG) to reduced glutathione (GSH). Solution of GSSG is contained by a prepared micro test tube, microtiter plate or a microfluidic chip. After the application of sample and a predetermined incubation time at 37° C. the amount of GSH is quantified. I may be carried out by using fluoro- or chromophore dye staining the free sulfhydryl groups. Readily available kits exist (see http://www.abcam.com/gshgssg-ratio-detection-assay-kit-fluorometric-green-ab138881.html, https://worldwide.promega.com/products/cell-health-and-metabolism/oxidative-stress-assays/gsh_gssg_glo-assay/). Quantification may be based on absorbance, colorimetry or fluorometry using a chip reader, or plate reader. The reaction can also be quantified using colorimetry where the labeling dye is bound to a test strip, to which a droplet of incubated (in a micro test tube for eg.) sample/glutathione solution is applied.

The vast majority of currently used in vitro embryo culturing media contains serum proteins as these molecules are a crucial, seemingly irreplaceable component. In case of human embryos, the serum proteins used are conventionally proteins derived from human serum. Macromolecular supplementation of culture media, in the form of whole serum, isolated serum proteins, recombinant serum proteins, or alternative polymers provides both chemical and physical interface of embryos with their microenvironment and are crucial for maximizing embryonic viability (19). The role of macromolecular supplementation of the human embryo culturing media is described in detail by e.g. Patrick Quinn: Culture Media, Solutions, and Systems in Human ART, Cambridge University Press, 2014. (19) and in Manual of Assisted Reproductive Technologies and Clinical Embryology, JP Medical Ltd, 2012 (20).

The concern regarding diseases transmissible by the use of protein obtained from donors (e.g. prion-associated diseases) in the culture media of human embryos has lead to several attempts to substitute donor derived serum and serum proteins and also to the development of protein free media (PFM). The use of recombinant proteins (e. g. albumin) has been suggested (21). EP 2 235 160 describes a substantially protein free culture medium to be used in in vitro fertilization and other assisted reproduction technologies in humans. However, the use of these alternative media has remained marginal to the date of this application.

Conventionally used embryo culturing media contain human serum albumin (HSA) as a growth promoting agent. HSA is most often purified from donor serum and it is a described fact that during purification several other polypeptides such as haptoglobin can accumulate in commercially available standards (14). We have investigated how different batches of the HSA standard affect the initial haptoglobin alpha-1 fragment content of the medium. The variation found was much lower than the difference expressed as a percentage between the viable and non-viable embryo groups.

During the discovery phase of our study (n=10) a novel polypeptide marker was found which showed a significant differences (p<0.001) in quantity between the successful and unsuccessful embryo groups. This molecule was identified with tandem mass spectrometry as the alpha-1 fragment of human haptoglobin. Detection and quantitation of the alpha-1 haptoglobin fragment of the culture medium proved to be a good additional method to the conventionally used microscopic inspection. The method of the invention identifies non-viable embryos which—in spite of their promising microscopic morphology—should not be implanted. Using the method of the invention, we were able to select with 100% accuracy the embryos with zero potential to result in pregnancy. In this group the observed increased amount of the 9186.5 Da haptoglobin fragment proved to be a quantitative indicator of negative prediction prior embryo transfer. The combination of microscopic evaluation with the measurement of the haptoglobin fragment increases the success rate to 50%.

According to our results, the determination of the amount of the human haptoglobin alpha-1 fragment in a sample of the culture media of embryos prior transfer and comparing the amount of said fragment to blank control samples incubated together with the embryos under the same circumstances may provide a more accurate non-invasive embryo viability assessment to increase the success rate of IVF processes.

Detection of the amount of fragments of the haptoglobin molecule in samples of the culture media may be achieved by various protein/peptide detecting methods known in the art. Such methods include e. g. spectrometric and spectroscopic procedures, such as mass spectrometry.

For example, MALDI-TOF mass-spectrometry has become a popular tool. High throughput and relative simplicity of this technology have made it attractive for biomarker discovery and validation. Furthermore, technical approaches have been developed for protein-chip based SELDI-TOF mass-spectrometry (22), see US 2003/0017515A1. Such methods can be accompanied by purification techniques to enrich the sample in the haptoglobin fragment. Such techniques involve purification with magnetic beads, chromatographic methods, such as liquid chromatography, etc. In mass spectrometry peak area may correlate with concentration.

A further preferred option involves different immunoassays, such as Western blot, radio-immune assay, ELISA, sandwich enzyme-linked immunosorbent assay, etc.

Immunoassay typically use antibodies. In the present invention, analogously, other binding molecules like antibody mimetics can be used. A requirement for antibodies and binding molecules like antibody mimetics to be used in the present invention is that it should be capable of recognizing the haptoglobin fragment to be detected and differentiate it from the whole haptoglobin or a fragment thereof which is not to be detected in the assay setup. For example binding molecules like antibodies specific against the alpha or beta chains can be used (23).

Ready-made antibodies against both the alpha and the beta chains are commercially available for the above mentioned detection methods. Antibodies against the intact haptoglobin molecule are also available commercially (Abcam, Randox LifeSciences, Santa Cruz Biotechnology, Acris Antibodies GmbH etc.). The combined use of an antibody against either the alpha or the beta chain and against the intact haptoglobin may enhance the accuracy of the quantification measurements. Manufacturing of tailor made antibodies is also extensively described in the literature and is well within the knowledge of the skilled artisan.

A detailed description of the techniques which may be used when carrying out the method of the invention is found e.g. in The Immunoassay Handbook, Fourth Edition: Wild D: Theory and applications of ligand binding, ELISA and related techniques Elsevier Science; 4. edition, 2013 and in Gosling, J P Immunoassays: A Practical Approach Oxford University Press; 2000 (24 and 25).

These methods may be combined with fast sequencing method allowing a specific detection of antibody chains.

Thus, such antibodies or binding molecules can be used in kits for assessment of viability of embryos for the purpose of in vitro fertilization methods. Such a kit may also comprise a culture media or components thereof for culturing embryos as well as control media, haptoglobin standard or compositions comprising such haptoglobin standard Haptoglobin standard preferably comprises a fragment thereof to be detected and/or other fragments or haptoglobin itself as controls which are not to be detected. Means for separation of haptoglobin fragments may be included as well.

It is possible to use the method of the invention even in ART processes where the culture medium is supplemented with non-serum derived albumin or the culture medium is a protein free medium. Haptoglobin may be added to such media after fertilization as a biochemical marker without the risk of interfering with the development of the embryo.

EXAMPLES

Materials and Methods

Patients

Our study was performed between Mar. 24, 2013 and May 9, 2013 in the Assisted Reproduction Unit, Department of Obstetrics and Gynecology, University of Pécs, Hungary. In this period we started 90 unselected IVF cycles and we made transvaginal ultrasound guided aspiration of follicular fluid. The patients participated in our IVF program were aged 23-40 years (mean: 32.3±5.1 years) and had BMI of 21.3-29.7 (mean: 23.80±1.9). They presented with the following main infertility diagnosis: male factors (14, 33.3%), damaged or blocked Fallopian tubes (10, 23.8%), severe endometriosis (7, 16.7%) and unexplained infertility (11, 26.2%). These latter patients experienced six unsuccessful intrauterine inseminations previously. The patients were collected into this study according to the date of the procedure, so it was an unselected population. Among the patients there were no individuals with known diabetes mellitus (type I and II), or reduced glucose tolerance.

Study Protocol

GnRh agonist triptorelin (Gonapeptyl; Ferring®, Germany) was used in a long or short protocol, and the stimulation was performed with individual dosages of rFSH (Gonal-F; Serono® Aubonne, Switzerland), varying from 100 to 225 IU per day depending on the follicular maturation. The starting dose was adapted according to the BMI and the age. For patients with a previously known low response it was increased to a maximum dose of 300-350 IU daily. The follicular maturation was determined by ultrasound examination from the 6th day of the cycle, every other day. We changed the amount of the administered gonadotropins individually according to the size of the follicles. Ovulation was induced by injection of 250 ug of hCG (Ovitrelle; Serono® Aubonne, Switzerland) when at least two follicles exceeded 17 mm in diameter, and aspiration of follicular fluid was performed 36 hours later by ultrasonography-guided transvaginal puncture under routine intravenous sedation. The oocyte collection was performed using a Sonoace 6000C two dimensional real time ultrasound scanner equipped with 4-8 MHz endovaginal transducer. The oocyte collection was performed in G-MOPS™ medium (Vitrolife, Göteborg, Sweden).

Fertilization Methods

We performed the fertilization with Intracytoplasmatic Sperm Injection (ICSI) depending on the andrological status (sperm count less than 15 M/ml), the maternal age (>35) and the number of the previous IVF cycles the patient had before (>2). The oocytes selected for ICSI were denuded with hyaluronidase and were assessed for maturity. Only metaphase II oocytes, identified by the presence of the first polar body, were chosen for fertilization. ICSI was performed 3-6 h after oocyte recovery in the medium G-MOPS™. The remained oocytes were fertilized with the conventional IVF method in a bicarbonate buffered medium (G-IVF™, Vitrolife®, Göteborg, Sweden). Fertilization was assessed 24 hours later in the medium G-1™ v5 (Vitrolife®, Göteborg, Sweden).

Embryo transfers were done 3 or 5 days after the oocyte retrieval. From day 3 to blastocyst stage we use the medium G-2™ v5 (Vitrolife®, Göteborg, Sweden) supplemented with human serum albumin (HSA, Vitrolife®, Göteborg, Sweden) in a 5 mg/ml concentration. According to the patient request we transfer one, two or three embryos. Cryopreservation of the remaining embryos was performed at this stage according to the Hungarian law. Progestogen supplementation was provided using 300 mg of progesterone 3 times a day (Utrogestan; Lab. Besins International S.A.®, Paris, France). To evaluate the success of the treatment transvaginal ultrasound examination was performed 21 days after the embryo transfer to detect gestational sac. After the transfer culture medium samples were kept at −24 C in 40 μl aliquots until the measurement.

Proteomics Analysis

Unused culture medium was chromatographed on Aeris Peptide HPLC column (2.1×150 mm) using gradient elution and fractions were collected. Fractions containing proteins of interest were constructed of 10 consecutive runs and were lyophilized. Protein(s) in this pooled sample was identified by proteomics method. Disulfide bridges were reduced (DTT) and alkylated (iodoacetamide) and polypeptides were digested with trypsin [1]. Peptides in the reaction mixture were separated by nanoHPLC on an EASY-column (75 μm×100 mm, C18-3 μm, Thermo Scientific) and analyzed by an online connected a MAXIS 4G QTOF mass spectrometer equipped with captive spray ESI ionsource (Bruker, Bremen). The mass spectrometer was operated in data dependent analysis (DDA) cycling mode to automatically collect MS/MS fragmentation spectra of the 3 most abundant ions in every MS scan. Raw data files were processed and MS/MS peaklists were produced in Bruker DataAnalysis 4.0. Peaklists were submitted for protein identification to Mascot 2.4 (Matrixscience,) using Bruker Proteinscape 2.1. Swissprot database (version 2013.10, containing 541,561 sequences) was used for identification. Additional searches were performed on an in house created database, which contained all variants of HPT_HUMAN and HPTR_HUMAN proteins. Search parameters used in all cases for identification were: 120 ppm and 0.25 Da precision for parent mass and fragment spectra, respectively. Trypsin as digestion enzyme (assuming max. 2 missed cleavage sites), carbamidomethylation of cysteins as fixed, and oxidation of methionines as variable modifications were used for data analysis. Identified MS/MS spectra were manually validated using Bruker Biotools 3.2 software.

Solvents and Preparation of Internal Standard and Samples

All solvents used for internal standard solution and HPLC solvent preparation were of LC-MS grade, purchased from Molar Chemicals (Molar Chemicals, Hungary). Water, acetonitrile, and formic acid were used in the HPLC solvents.

Cortisol (Sigma-Aldrich, Budapest, Hungary) was used as internal standard; a 3.86 μm/L solution was prepared in 20% methanol. After thawing the culturing media solutions, to every 25 μl of media 5 μl of IS solution was added and was vortex mixed for five seconds. The injection volume was 20 μl.

LC-MS Conditions

A Dionex Ultimate 3000 (Dionex Corp., USA) analytical HPLC equipped with an autosampler and a column thermostat set at 30° C. was used. Separation was carried out on a Kinetex C18 2.6 μm, 2.1×100 mm analytical column (Phenomenex, USA) with a multi-step gradient elution at a flow rate of 200 μL/min. HPLC solvents contained 0.1% formic acid in 5% (A) and 95% (B) acetonitrile in water. The gradient profile is described in Table 1; the total runtime is 27 minutes.

TABLE 1

Description of the HPLC gradient used in the LC-MS run.

| Time (minute) | A % | B % |
|---|---|---|
| 0.0 | 100 | 0 |
| 16.0 | 60 | 40 |
| 20.0 | 0 | 100 |
| 21 [a] | 100 | 0 |

[a] At the end of every chromatographic run a six minute re-equilibration phase was inserted to start the new run at 100% „A" solvent concentration.

The mass spectrometer coupled to the HPLC was a Bruker micrOTOF accurate mass instrument equipped with an electrospray ionisation source (ESI) operated in the positive mode. Main source parameters were: capillary voltage: 4500V, nebuliser pressure: 2.4 bar, drying gas ($N_2$): 8 L/min and drying temperature: 210° C. Mass spectra were collected between 500 m/z and 1500 m/z. Internal mass calibration was performed at the beginning of every run using the peaks of $Na^+$ formate clusters.

Statistics

All statistical analysis was made using the IBM SPSS Statistics Version 20 (IBM Magyarország Kft. Budapest, Hungary) software. Normality of the dataset was investigated using the Kolmogorov-Smirnov test, while the differences in the amount of the peptide fragment between the experimental groups (incubated blank medium, successful and unsuccessful embryos) by analysis of variance (ANOVA) and Student's t-test.

Example 1. Identification of Proteins in the Culture Medium

Chromatographic conditions of the applied gradient are summarized in Table 1. Our primary aim was to find any qualitative or quantitative difference between incubation media of successful and unsuccessful embryos. This was done by measuring a smaller number of culture media samples of embryos transferred on day 3 (n=10) and embryos transferred on day 5 (n=10), all with known clinical outcome. Half of the samples were from successful and half from unsuccessful embryos. As control, empty incubated G-1™ v5 (3 day transfer) or G-2™ v5 (5 day transfer) containing 5 mg/ml HSA was used (n=4). The incubation of the control samples were done parallel with the embryos under the same circumstances and time interval. Qualitative differences were not found, however four different polypeptides were detected which all notable differed in quantity between the two embryo groups. These molecules were also present in the blank control samples however absent from the G-1™ v5 and G-2™ v5 containing no HSA. The compounds were detected at m/z 798.9 $[M+6H]^{6+}$, m/z 745.1 $[M+6H]^{6+}$, m/z 771.9 $[M+6H]^{6+}$ and m/z 1149.3 $[M+8H]^{8+}$. Deconvolution of the obtained mass spectra revealed that the monoisotopic masses of the four molecules are 4787.4 Da, 4464.6 Da, 4622.4 Da and 9186.5 Da respectively. Quantification was done using the peak areas (without unit of measurement) of the corresponding ion chromatographic peaks. Peak areas of the detected compounds were standardized using the summarized peak areas of the $H^+$ and $Na^+$ adduct ions of the IS cortisol. We found that the compounds were present in the samples of unsuccessful embryos in a 30-60% larger extent than in the samples of the successful embryos, or the control samples. No notable difference was observed however between the control samples and the samples of the successful embryos. Similar observation was made in the case of 3 day and 5 day embryos, though in the latter case the difference was only 10-30% depending on the selected compound. To find out whether the observed difference was significant, Student's t-test was performed which revealed that only the 9186.5 Da molecule differs significantly in its amount between the two embryo groups (p=0.005). For this reason we further concentrated only on the 9186.5 Da molecule (FIG. 1).

The next step was the MS/MS identification of the polypeptide according to the protocol described in the materials and methods section. Database search using MS/MS data identified two peptide fragments assigned to human haptoglobin. According to manual investigation of sequence annotations of database entries and literature data the protein of interest identified by the two MS/MS fragments proved to be the haptoglobin alpha-1 chain. This form of haptoglobin alpha-1 subunit has a monoisotopic mass of 9186.4; all identified sequences correspond to this region of the haptoglobin precursor protein. The overall sequence coverage of the identification was 62%. The complete sequence of the haptoglobin alpha-1 fragment with the two identified MS/MS fragments with significant hits is summarized in Table 2.

TABLE 2

Identification of peptides assigned to haptoglobin alpha-1.
Underlined sequences correspond to the two significantly
identified MS/MS fragments of the polypeptide. Identification
was carried out on an in-house built database of human
haptoglobin variants.
P00738 (HPT_HUMAN) Haptoglobin VAR_017112
[19-102] (Haptoglobin alpha-1)

VDSGNDVTDIADDGCPKPPEIAHGYVEHSVRYQCKNYYKLRTEGDGVYTLNDEKQWINKAVGDKLP
ECEAVCGKPKNPANPVQ

| Start - End | Observed | Mr(expt) | Mr(calc) | Mascot Score | Expect Value | Peptide Sequence |
|---|---|---|---|---|---|---|
| 42 - 54 | 720.9006 | 1439.787 | 1439.642 | 88 | 1.50E-09 | R.TEGDGVYTLNDEK.Q |
| 60 - 76 | 620.043 | 1857.107 | 1856.912 | 58 | 1.60E-06 | K.AVGDKLPECEAVCGKPK.N |

Example 2. Determination of the Viability of Embryos by Measuring the Human Haptoglobin Alpha-1 Fragment The blinded analysis that was performed after the identification of the fragment was performed on a number of 80 samples of embryos transferred on the third day. The analysis was performed on a larger number of culture medium samples, composed of samples of embryos with unknown clinical outcome (n=80) and blank control samples (n=10). Only peaks corresponding to the two adduct ions of the IS ([M+H]$^+$ and [M+Na]$^+$) and to the [M+8H]$^{8+}$ ion of the haptoglobin alpha-1 fragment were integrated. In this phase only samples of the embryos transferred on the third day and G-1™ v5 controls were measured since transfer on day three is more common and the same phenomenon was observed in both sample groups (day 3 and day 5 embryos, G-1™ v5 and G-2™ v5 controls). Further it is better to assess embryo viability in the possibly earliest stage of the pre-implantation development.

Figure 2:
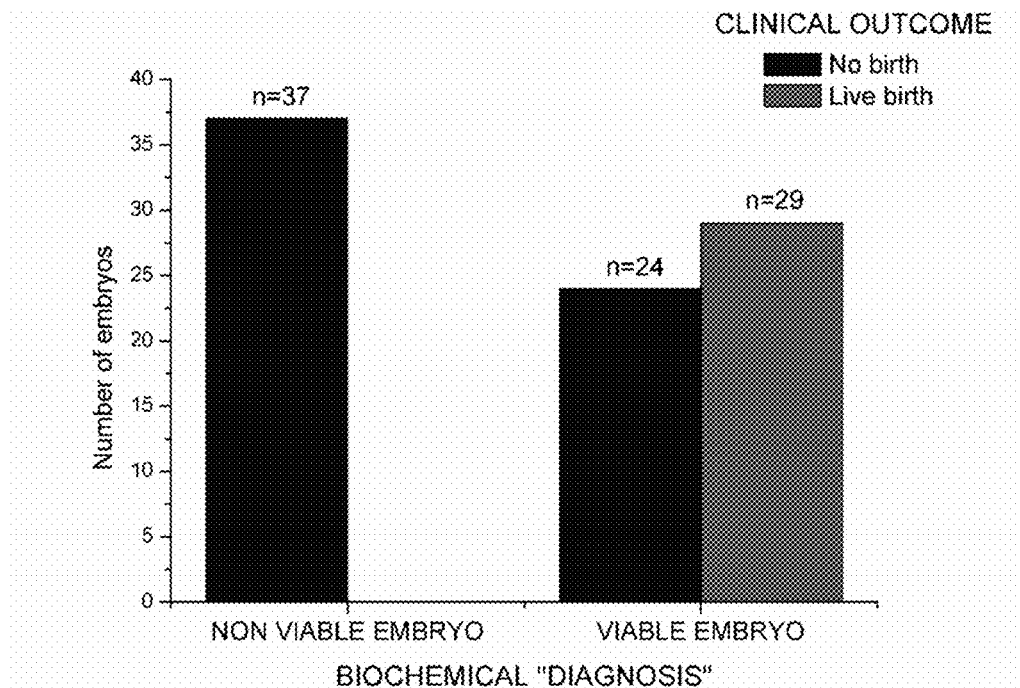
FIG. 2 Results of the blinded analysis of embryo culture medium after three days of incubation (n=80).

Data from this set of measurements was used parallel for two approaches, first to build a statistical database, and second to test the reliability of our method. The latter was done by the blind analysis of coded samples which was only resolved after the measurement was complete, and a biochemical "diagnosis" had been established whether the embryo possibly belonged to the viable or to the non-viable group. The values of raw peak area data of the samples were compared to the values measured in empty control medium incubated under similar circumstances as the samples containing embryos. If the peak area of the haptoglobin fragment was under the 120% value measured in the blank control, the sample was classified as viable. This threshold was established empirically. If the measured value was above the 120% of the control, the embryo was classified as non-viable. Among the 80 samples 32 were found to be non-viable by the biochemical characterization and 48 proved to be viable. From the 32 embryos classified as non-viable there was not a single case where the transfer resulted in successful delivery. In the group where the embryos were classified as viable the birth rate was 54% (FIG. 2.). During our sample collection period only three pair of twins were born, in their case both transferred embryos were classified biochemically as viable.

Figure 3:
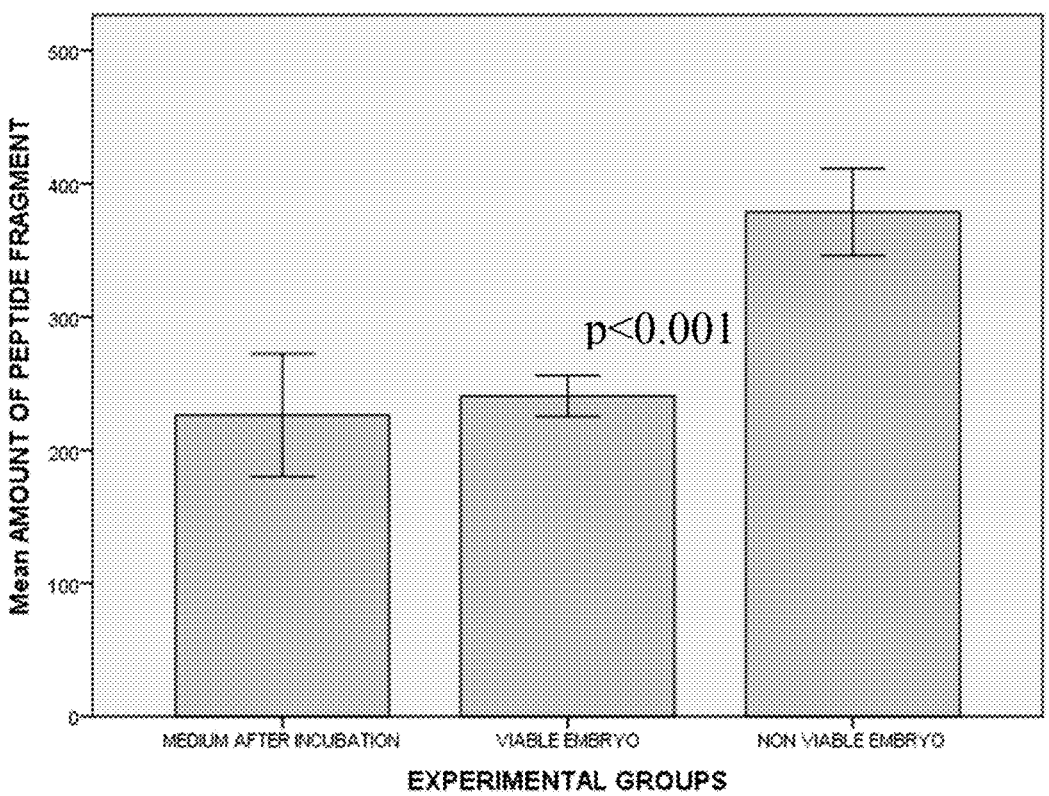
FIG. 3 Bar chart of the mean amount of the haptoglobin alpha-1 fragment amount in the control (n=12), viable embryo and non-viable embryo samples (total n=90). A significant difference (p<0.001) was found between the non-viable embryo and the other two groups.
Figure 4:
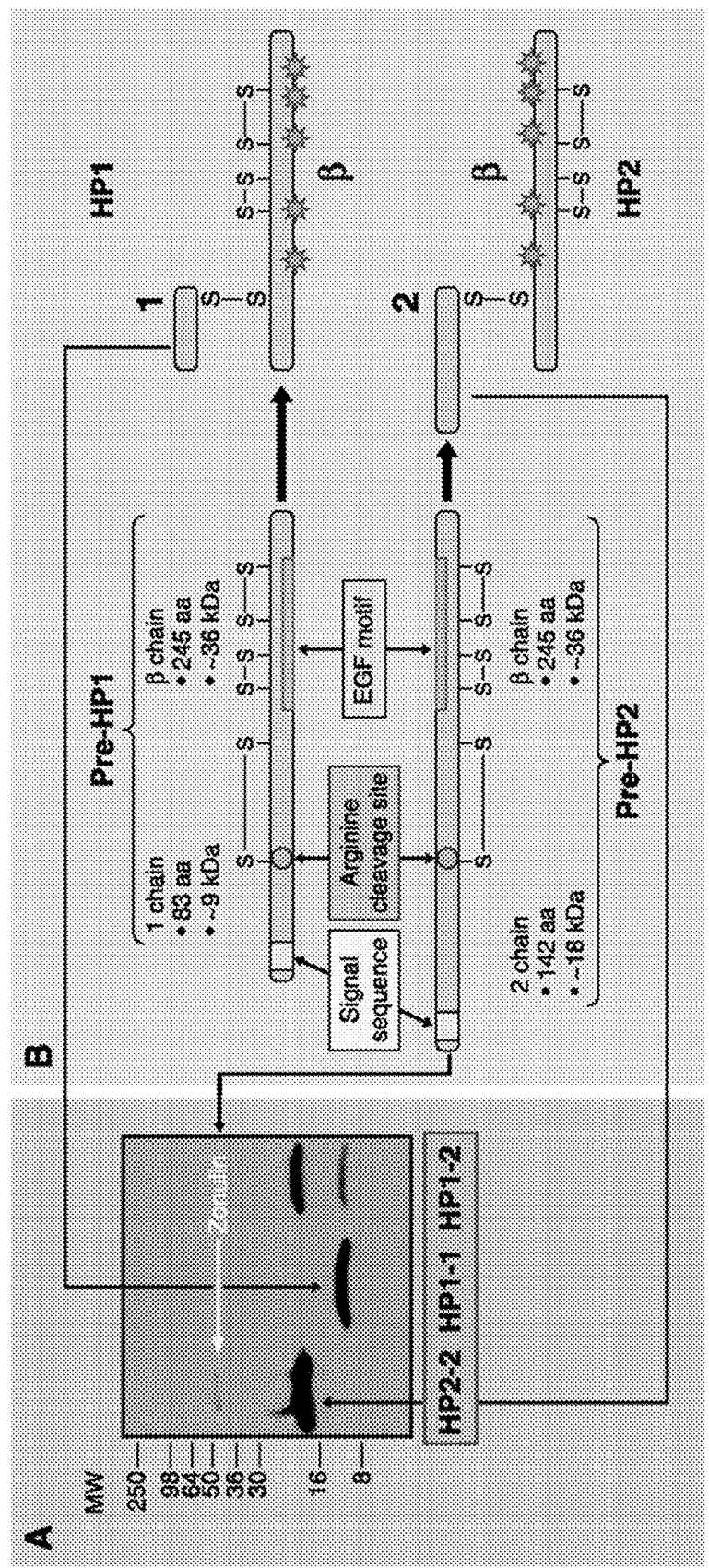
FIG. 4 A: Western blot of zonulin cross-reacting anti-Zot polyclonal antibodies showing a 18-kDa immunoreactive band and a fainter ~45-kDa band (lane 1), sera showing only a 9-kDa band (lane 2), and sera showing both the 18- and 9-kDa bands (lane 3). B: schematic showing the structure of both pre-haptoglobin (HP) 1 and pre-HP2 and their mature proteins (on the far right side). Pre-HPs are translated as single-chain precursor proteins. Pre-HPs may be proteolytically cleaved intracellularly into α- and β-chains that remain disulfide linked, referred to as cleaved, two-chain mature HPs.

Statistical analysis of the results involved 90 embryo samples and 12 incubated blank control samples. We also investigated how different batches (n=10) of HSA affect the initial haptoglobin alpha-1 content of the culture medium. Normality of the data was tested using the one-sample Kolmogorov-Smirnov test, which revealed a normal distribution. Afterwards average values and standard deviation of the haptoglobin alpha-1 fragment amount was calculated for the controls, the different culture medium batches and all the measured embryo samples (n=90) with viable (n=55) and non-viable outcome (n=35). Correlation analysis of the amount of the peptide fragment with the diagnosis established during the blind measurements, and analysis whether significant differences exist or not between the viable embryo, non-viable embryo and blank control groups were examined using the ANOVA test. The average value of the haptoglobin fragment was 226.4 (CV 7.9%) in the control samples while 240.9 (CV 23.5%) in the samples of the viable embryos and 378.8 (CV 25.4%) in the samples of the non-viable embryos. The ANOVA test revealed a significant difference between the two embryo groups (p<0.001) and a significant correlation (p<0.001) between the amount of the peptide fragment and the pregnancy outcome. The quantified difference between these two groups was 57.2% (FIG. 3.). A significant difference was also observed (p<0.001) between the incubated control medium group and the non-viable group, while there were no difference between the incubated blank control and the viable group Blank medium samples were measured before and after incubation, but no significant difference was observed. As control however incubated blank medium samples were used.

Ten different batches of culture media were also measured after concurrent incubation under the same circumstances. These measurements were not included among the controls used in the above-described statistics. The average value of the haptoglobin alpha-1 fragment peak area in the ten media from different batches after incubation was 257.3 (CV 8.9%). The minimum peak are value was 213 while the maximum 283 (data not presented).

Example 3. Determination of the Viability of Embryos by Measuring the Reducing Potential of the Spent Embryo Culture Medium The analytical standards of glutathione disulphide (GSSG), glutathione (GSH) and mercapto-succinic acid was purchased from Sigma-Aldrich Kft. (Budapest, Hungary). Mercapto succinic acid was not available as a disulphide; the solution of the reduced form was subjected to air oxidization (26), a disulphide forming spontaneous reaction of any compound containing thiol groups. The efficiency of this reaction was detected by direct electrospray ionization (ESI) mass spectrometry. The mercapto-succinic acid solution used in the experiments contained 84% mercapto succinic acid disulphide and 16% of the original reduced form.

To 25 µl of the previously described spent culture media of viable (n=10) and non-viable (n=10) embryos 5 µl of 8 µmol/µl solution of GSSG (40 µmol), or µl of 7.5 pmol/µl solution of pmol mercaptosuccinic acid (34.6 pmol disulphide and 2.9 pmol reduced form) was added. For control empty G1+HSA solution (n=5+5) served prepared in the same way. In order to prevent auto-oxidation of GSH (27), or the reduced mercapto succinic acid 100 pmol of sodium thiosulphate was added to every solution. The solution were incubated for three days, under conditions identical to the in vitro fertilized embryos. After incubation the samples were measured by liquid chromatography coupled mass spectrometry (LC MS), cortisol was used as internal standard.

Figure 5:
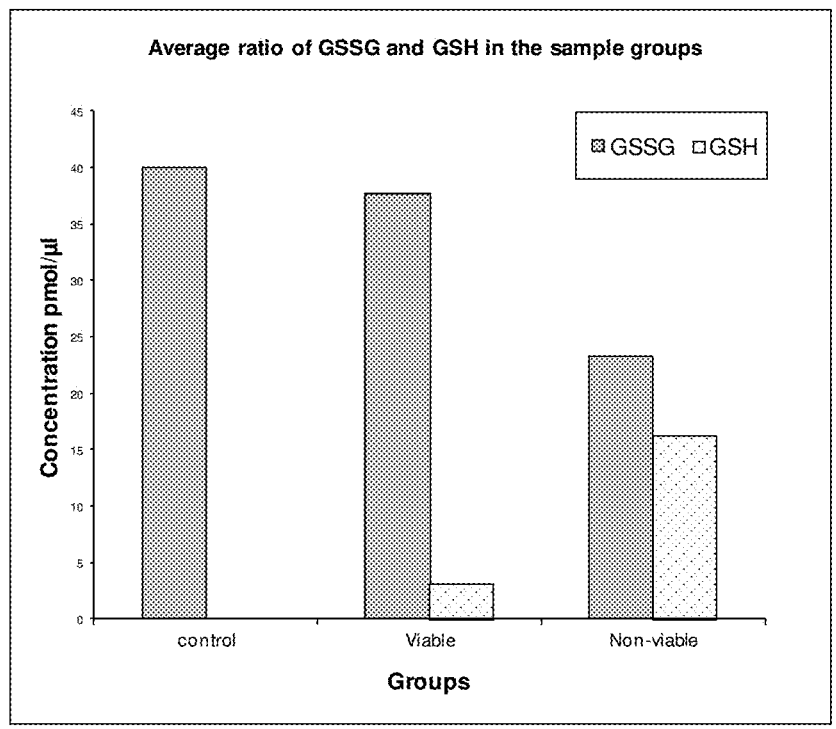
FIG. 5 Bar chart of the experiments where GSSG (panel A) and oxidized mercapto-succinic acid (panel B) was incubated in the embryo culture medium for three days. Note that the solution of oxidized mercapto-succinic acid had only a 84% purity, containing 16% of reduced mercapto-succinic acid.
Figure 5:
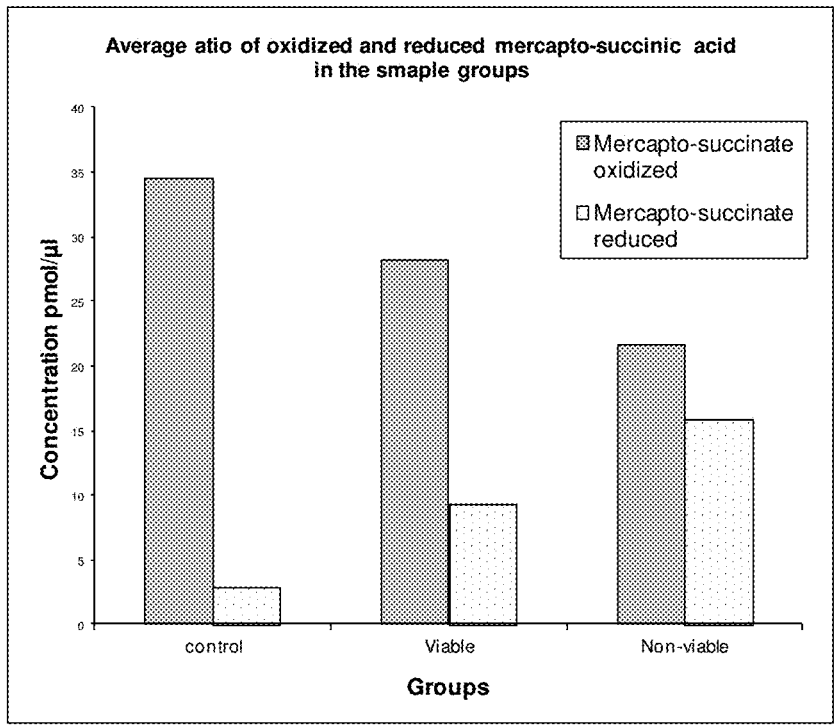

Results:

LCMS measurements revealed that after three days of incubation there was a significant decrease of GSSG (p=0.001) or mercapto-succinic acid disulphide (p<0.001) in the samples of the non-viable embryo group compared to the control or the viable group. In parallel to that a quantitative increase in the amount of GSH and reduced mercapto-succinic acid was also observed. Results are summarized on FIG. 5. The quantified difference in the amount of GSSG in the samples of the non-viable group was 29% less compared to the viable and 37% less to the control group. The quantified difference in the amount of oxidized mercapto-succinic acid was 25% less compared to the viable and 35% less to the control group.

CONCLUSIONS

The specificity of the reaction potential responsible for reducing the disulphide bond within the haptoglobin molecule resulting in the increased formation of the alpha-1 fragment is not only confined to haptoglobin, but to other disulphides as well. Under current clinical circumstances, however, these reactions cannot be used to assess embryo viability directly, since the use of sodium-thiosulphate, an oxygen binding reagent does not allow to detect these reactions as indicators of embryo viability. In oxygen depleted environment mammalian cells can not develop, not yet to mention the unknown consequences of additional compounds being present in the approved incubation medium. Without the use of sodium-thiosulphate both compounds tend to go under auto-oxidation during incubation time masking the disulphide bond reduction. For some reason, the reduced disulphide bond within the haptoglobin molecule connecting the haptoglobin alpha-1 chain with the rest of the protein does not tend to auto-oxidate, the formed alpha-1 fragment stays stable within the embryo culture medium.

However, the format as described in this example is readily adaptable to real life assays. Although the present example used 3-days incubation time, further experiments were carried out with significantly shorter incubation periods (data not shown) which will enable the present method to be applied in actual clinical settings.

INDUSTRIAL APPLICABILITY

The invention relates to in vitro methods for non-invasive embryo viability assessment during assisted reproduction. The solution is suitable to increases the pregnancies and birth rates in in vitro fertilization methods.

REFERENCES

1. Ferraretti A P, Goossens V, Kupka M, Bhattacharya S, de Mouzon J, Castilla J A et. al. European IVF-monitoring (EIM); Consortium, for The European Society of Human Reproduction and Embryology (ESHRE). Assisted reproductive technology in Europe, 2009: results generated from European registers by ESHRE. Hum Reprod 2013; 28:2318-31.
2. Fancsovits P, Toth L, Takacs Z F, Murber A, Papp Z, Urbancsek J. Early pronuclear breakdown is a good indicator of embryo quality and viability. Fertil Steril 2005; 84:881-7.
3. Dawson K J, Conaghan J, Ostera G R, Winston R M, Hardy K. Delaying transfer to the third day post-insemination, to select non-arrested embryos, increases development to the fetal heart stage. Hum Reprod 1995; 10(1):177-82.
4. Scott R, Seli E, Miller K, Sakkas D, Scott K, Burns D H. Noninvasive metabolomic profiling of human embryo culture media using Raman spectroscopy predicts embryonic reproductive potential: a prospective blinded pilot study. Fertil Steril 2008; 90:77-83.
5. Kovalevsky G, Patrizio P. High rates of embryo wastage with use of assisted reproductive technology: a look at the trends between 1995 and 2001 in the United States. Fertil Steril 2005; 84:325-30.
6. Botros L, Sakkas D, Seli E. Metabolomics and its application for non-invasive embryo assessment in IVF. Mol Hum Reprod 2008; 14:679-90.
7. Cortezzi S S, Cabral E C, Trevisan M G, Ferreira C R, Setti A S, Braga D P et. al. Prediction of embryo implantation potential by mass spectrometry fingerprinting of the culture medium. Reproduction 2013; 145:453-62.
8. Wrenzycki C, Herrmann D, Niemann H Messenger RNA in oocytes and embryos in relation to embryo viability. Theriogenology 2007; 68(Suppl 1):775-83S.
9. Singh R, Sinclair K D. Metabolomics: approaches to assessing oocyte and embryo quality. Theriogenology 2007; 68(Suppl 1):56S-62S.
10. Gardner D K, Wale P L. Analysis of metabolism to select viable human embryos for transfer. Fertil Steril 2013; 99:1062-72.
11. Polticelli F, Bocedi A, Minervini G, Ascenzi P Human haptoglobin structure and function a molecular modelling study. FEBS J 2008; 275:5648-56.
12. Cigliano L, Spagnuolo M S, Abrescia P. Quantitative variations of the isoforms in haptoglobin 1-2 and 2-2 individual phenotypes. Arch Biochem Biophys. 2003 416: 227-37.
13. Fasano A. Zonulin and its regulation of intestinal barrier function: the biological door to inflammation, autoimmunity, and cancer. Physiol Rev. 2011, 91:151-175.
14. Darcel C L, Kaldy M S. Further evidence for the heterogeneity of serum albumin. Comp Biochem Physiol B 1986; 85:15-22.
15. Fasano A. Zonulin and its regulation of intestinal barrier function: the biological door to inflammation, autoimmunity, and cancer. Physiol Rev 2011; 91:151-75.
16. Ye, Bin et al., Haptoglobin-Subunit As Potential Serum Biomarker in Ovarian Cancer: Identification and Characterization Using Proteomic Profiling and Mass Spectrometry. Clinical Cancer Research, 9, (2003) 2904-2911.

17. Keegan D A et al: "P-229", Fertility and Sterility, 86, (2006), 5219
18. Brill A, Torchinsky A, Carp H, Toder V. The role of apoptosis in normal and abnormal embryonic development. J Assist Reprod Genet 1999; 16:512-9.
19. Quinn P Culture Media, Solutions, and Systems in Human ART Cambridge University Press, 2014.
20. Manual of Assisted Reproductive Technologies and Clinical Embryology JP Medical Ltd, 2012
21. Bungun M, Humaidan P, Bungum L. Recombinant human albumin as protein source in culture media used for IVF: a prospective randomized study Reproductive BioMedicine Online 20024 (3) 233-236
22. Karpova, M A, Moshkovskii, S A, Toropygin, I Y and Archakov, A I, Cancer-specific MALDI-TOF profiles of blood serum and plasma: Biological meaning and perspectives. Journal of Proteomics 73 (2010) 537-551
23. Gebauer M, Skerra A. "Engineered protein scaffolds as next-generation antibody therapeutics". Curr Opin Chem Biol 13 (3) (June 2009) 245-255.
24. Wild D. The Immunoassay Handbook, Fourth Edition: Theory and applications of ligand binding, ELISA and related techniques Elsevier Science, 2013
25. Gosling, J P Immunoassays: A Practical Approach Oxford University Press; 2000 (48, 49).
26. José Luis Garcia Ruano, Alejandro Parraa, José Alemána Efficient synthesis of disulfides by air oxidation of thiols under sonication. Green Chem., 2008 10:706-711.
27. Isabella Squellerioa, Donatella Carusob, Benedetta Porroa, Fabrizio Vegliaa, Elena. Tremolia, Vivian. Cavalcaa. Direct glutathione quantification in human blood by LC-MS/MS: comparison with HPLC with electrochemical detection. J Pharm Biomed Anal 2012 71:111-8.

The invention claimed is:

1. In vitro method for non-invasive embryo viability assessment comprising
   a) assessing the reducing potential of an embryo culture medium by detecting the reduction of a reducible compound added to said culture medium, said reducible compound being selected from the group consisting of haptoglobin, glutathione disulfide (GSSG), oxidized mercapto-succinic acid and oxidized mercapto-butanol wherein if the reducible compound is glutathione disulfide (GSSG), oxidized mercapto-succinic acid or oxidized mercapto-butanol, then said compound is added to the culture medium or a sample thereof only after removal of the embryo and in the presence of an oxygen binding reagent that prevents auto-oxidation thereof;

b) comparing said reducing potential to a predetermined reducing potential;

c) identifying the embryo cultured in said medium as being inappropriate for resulting in successful pregnancy, wherein said reducing potential is above said predetermined level.

2. The method according to claim 1, wherein said reducing potential is assessed in step a) by monitoring during culturing the embryo.

3. The method according to claim 1, wherein said reducing potential is assessed in step a) in a sample taken from the culture medium after the removal of the embryo.

4. The method according to claim 1, wherein said reducing potential is assessed in step a) by detecting the reduction of the reducible compound present in a sample of said culture medium and said reducible compound is human haptoglobin.

5. The method according to claim 4, wherein said sample taken in step a) is kept under conditions allowing said reducible compound to be reduced.

6. The method according to claim 4, wherein the reducing potential is indicated by a detectable amount of a reduced form of said reducible compound.

7. The method according to claim 4, wherein the reducing potential is assessed by detecting a reduced form of said reducible compound by spectrometric or spectroscopic procedure or by immunoassay.

8. The method according to claim 1, wherein said predetermined reducing potential is determined by
   i) culturing a pool of embryos in embryo culture medium;
   ii) assessing the reducing potential of the culture mediums of each embryos in said pool;
   iii) retrospectively correlating the reducing potential assessed in step ii) of each embryo culture medium to successful pregnancies resulted from implanting the embryos cultured in said culture medium; and
   iv) determining said predetermined reducing potential as the highest level of reducing potential wherein successful pregnancy was observed.

9. The method of claim 8 wherein said assessment in step ii) is done by detecting the reduction of a reducible compound and said highest level of reducing potential in step iv) is indicated by the non-detectability of the reduction of said reducible compound.

10. The method according to claim 1, wherein said reducible compound is haptoglobin.

11. The method according to claim 1, wherein the reducing potential is assessed by measuring the amount of a reduced form of said reducible compound present in the sample.

12. The method according to claim 11, wherein the reducing potential is assessed by quantifying the amount of alpha-1 subunit of human haptoglobin after separation from the sample.

13. The method according to claim 11, wherein the reduced form of said reducible compound is an alpha-1 fragment of human haptoglobin.

14. The method according to claim 1 wherein the reducible compound is glutathione disulfide (GSSG), oxidized mercapto-succinic acid or oxidized mercapto-butanol, said compound is added to the culture medium or a sample thereof only after removal of the embryo, and sodium thiosulphate is added to the culture medium.

15. A method comprising adding a reducible compound selected from the group consisting of haptoglobin, glutathione disulfide (GSSG), oxidized mercapto-succinic acid and oxidized mercapto-butanol, to embryo culture medium and subsequently measuring a detectable amount of a reduced form of said reducible compound in said culture medium or a sample thereof,
   wherein if the reducible compound is glutathione disulfide (GSSG), oxidized mercapto-succinic acid or oxidized mercapto-butanol, then said compound is added to the culture medium or a sample thereof only after removal of the embryo and in the presence of an oxygen binding reagent that prevents auto-oxidation thereof.

16. The method according to claim 15 wherein the reducible compound is glutathione disulfide (GSSG), oxidized mercapto-succinic acid or oxidized mercapto-butanol, said compound is added to the culture medium or a sample thereof only after removal of the embryo, and sodium thiosulphate is added to the culture medium.

* * * * *